(12) United States Patent
Han et al.

(10) Patent No.: US 8,857,434 B2
(45) Date of Patent: Oct. 14, 2014

(54) RETAINER CLIP FOR SECURING BREATHING DEVICES

(75) Inventors: Steve Han, Upland, CA (US); Steve Duquette, Laguna Niguel, CA (US); Terry Blansfield, Orange, CA (US); Terry Shum, La Palma, CA (US)

(73) Assignee: Carefusion 207, Inc., San Diego, CA (US)

( * ) Notice: Subject to any disclaimer, the term of this patent is extended or adjusted under 35 U.S.C. 154(b) by 1277 days.

(21) Appl. No.: 11/807,468

(22) Filed: May 29, 2007

(65) Prior Publication Data

US 2008/0295835 A1 Dec. 4, 2008

(51) Int. Cl.
*A62B 18/08* (2006.01)
*A61M 25/02* (2006.01)
*A61M 16/06* (2006.01)

(52) U.S. Cl.
CPC .......... *A61M 16/0683* (2013.01); *A61M 25/02* (2013.01); *A61M 2025/024* (2013.01); *A61M 16/0688* (2014.02)
USPC .................................................... 128/207.11

(58) Field of Classification Search
USPC ............ 128/207.11, 204.18, 207.17, 207.18, 128/206.11, 206.25, 200.24, 201.22, 128/202.27; 248/316.7
See application file for complete search history.

(56) References Cited

U.S. PATENT DOCUMENTS

| | | | | | |
|---|---|---|---|---|---|
| 4,480,639 | A | * | 11/1984 | Peterson et al. | 128/207.18 |
| 4,660,555 | A | * | 4/1987 | Payton | 128/207.18 |
| 4,742,824 | A | * | 5/1988 | Payton et al. | 128/207.18 |
| 4,774,946 | A | * | 10/1988 | Ackerman et al. | 128/207.18 |
| 5,117,818 | A | * | 6/1992 | Palfy | 128/204.11 |
| 5,271,391 | A | * | 12/1993 | Graves | 128/207.18 |
| 5,509,409 | A | * | 4/1996 | Weatherholt | 128/207.18 |
| 7,131,170 | B2 | * | 11/2006 | Weaver | 24/545 |
| 7,597,296 | B2 | * | 10/2009 | Conway | 248/229.16 |
| 2002/0157673 | A1 | | 10/2002 | Kessler et al. | |
| 2005/0075610 | A1 | | 4/2005 | Bierman | |

* cited by examiner

*Primary Examiner* — Tan-Uyen T Ho
*Assistant Examiner* — Colin W Stuart
(74) *Attorney, Agent, or Firm* — McDermott Will & Emery LLP

(57) ABSTRACT

A retainer clip configured to engage a tubing member includes a base portion and a clamp portion which may be formed as a unitary structure. The base portion is generally disc-shaped and has a front side and a back side. The clamp portion is disposed on the base portion and extends upwardly from the front side and includes a spaced pair of clamp fingers which collectively define a slot that opens into a channel. The channel is adapted to frictionally engage the tubing member. The back side includes a layer of adhesive for adhering the retainer clip to the patient such as to the patient's skin. An interface assembly for delivering gas from a gas source to a patient includes a user interface, at least one tubing member extending from the user interface, and at least one of the retainer clips configured to anchor the tubing member to the patient.

19 Claims, 1 Drawing Sheet

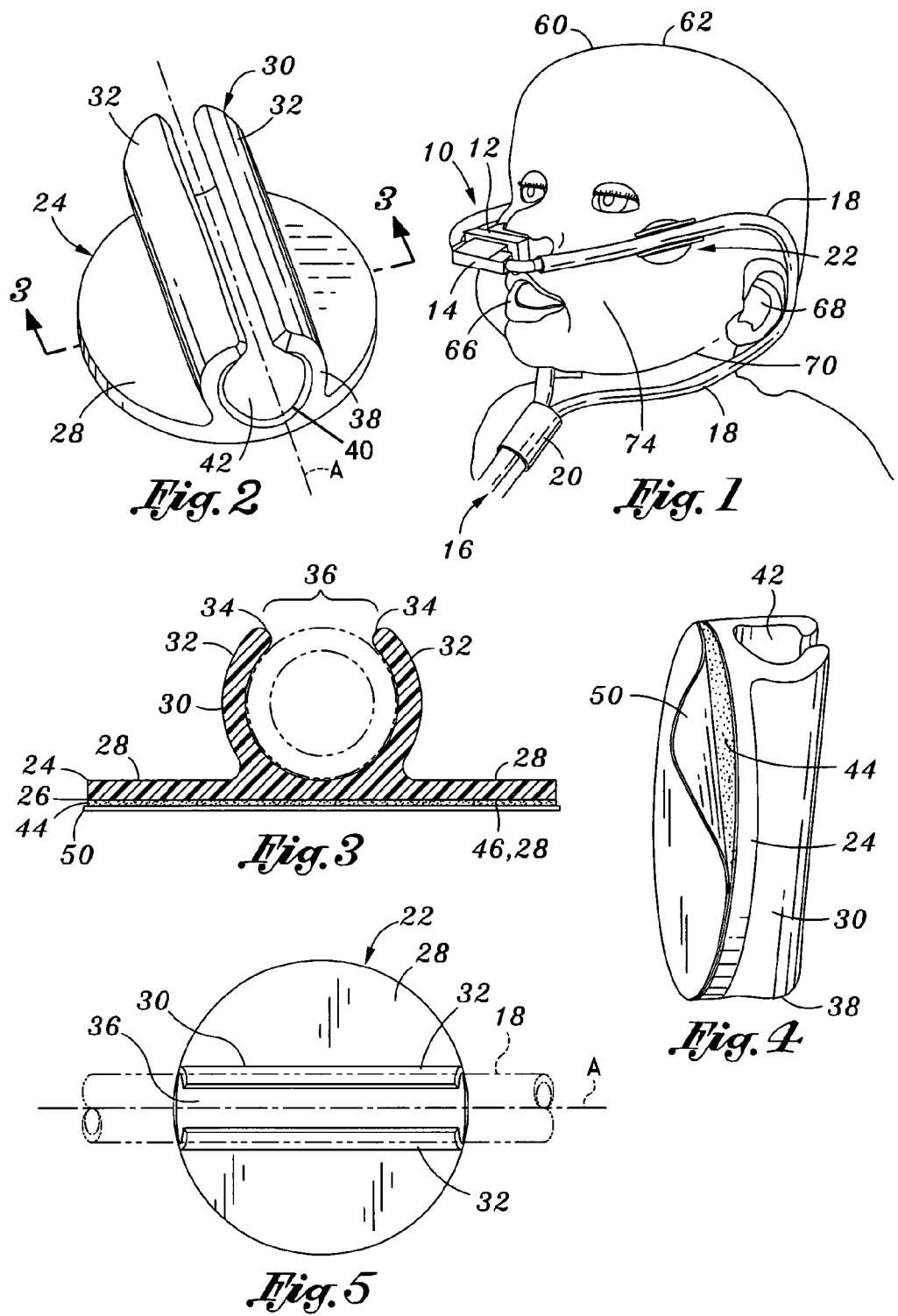

RETAINER CLIP FOR SECURING BREATHING DEVICES

CROSS-REFERENCE TO RELATED APPLICATIONS (Not Applicable)

STATEMENT RE: FEDERALLY SPONSORED RESEARCH/DEVELOPMENT (Not Applicable)

BACKGROUND

The present invention relates generally to breathing devices and, more particularly, to a uniquely-configured retainer clip that is specifically adapted to anchor a tubing member to a patient. The retainer clip assists in maintaining sealing engagement of a user interface (e.g., nasal mask, nasal cannula) to the patient by directly affixing the tubing member to the patient such as to the patient's cheek. The retainer clip assists in preventing dislodgement of the user interface as may occur in infants and neonates whose frequent head movements can compromise the sealing of the user interface or whose frequent handling by others such as during feeding can cause dislodgement of the user interface.

The use of breathing devices upon respiratory-impaired patients is well known. Generally, such apparatuses assist in patient breathing by allowing proper exchange of inhaled and exhaled gas and/or by delivering oxygen and/or medication to the patient. In one form of respiratory therapy, continuous positive airway pressure (CPAP) devices are specifically adapted to provide pressurized gasses to a patient's lungs while allowing spontaneous breathing by the patient.

CPAP devices typically include a gas source such as a blower unit which is connected to the user interface by a tubing member such as a gas supply tube. The user interface can be configured for invasive or non-invasive CPAP therapy wherein gas is ideally delivered to the patient at a constant and stable pressure. For invasive CPAP therapy, gas is delivered to the patient via a tracheal tube. For non-invasive CPAP therapy, gas is delivered to the patient's mouth and/or nose such as via a nose piece member or a face mask on the patient's head. The nose piece member may be integrally formed with the user interface or it may be a separate component.

Nose piece members (i.e., nasal masks, nasal pillows or plugs) are typically fabricated of a soft, elastic polymeric material which provides a comfortable surface to bear against the patient's skin. For nose piece members used in CPAP therapy, pressurized gas is directed into the patient's nostrils through a pair of nostril-engaging stems which are typically configured to anatomically conform to the interior of the patient's nostrils.

The ability to supply pressurized gas to the airways of a patient on a constant basis and at a stable pressure is critical in the effectiveness of CPAP ventilation. The application of constant CPAP therapy is especially important in treating certain respiratory complications in neonates such as respiratory distress syndrome (RDS). The proper application of CPAP ventilation is proven to be effective in developing and restoring respiratory capacity in neonates and infants.

Unfortunately, although prior art CPAP devices are generally effective in delivering respiratory therapy to a variety of patients including infants, such breathing devices possess certain deficiencies which detract from their overall effectiveness. These deficiencies are associated with user interfaces wherein CPAP therapy is delivered via mouth and/or nasal-based devices such as nasal masks, nasal prongs or nasal cannulae. For example, some of the prior art nasal masks and nasal prongs are secured to the patient using a system of straps which wrap around the patient's head in order to hold the user interface in position against the patient's nose such that a proper seal is maintained at the user interface.

Unfortunately, the system of straps is typically uncomfortable when worn for extended periods of time. If adjusted too tightly, the straps create excessive pressure at the user interface against the patient's face which is particularly problematic if the user interface is provided as a pair of nasal prongs. More particularly, if the straps are adjusted too tightly around the patient's head, the nasal prongs may be forced upwardly into the patient's nose which can result in irritation of the tender mucus tissue lining the patient's nostrils. In addition, overly-tightened straps can result in general patient discomfort as well as other health complications. The above-described scenario associated with strap over-tightening is especially problematic for neonates and infants who are incapable of communicating to a caretaker the nature of their discomfort.

The administration of CPAP therapy via nasal cannulae is considered by some to be a more comfortable alternative to nasal masks or mouth-based user interface devices. Furthermore, the use of nasal cannulae in CPAP therapy is better tolerated by neonates as compared to nasal masks. However, proper fitment and positioning of nasal cannulae on the patient is imperative because unlike invasive CPAP user interfaces (i.e., nasal masks, nasal prongs, face masks) which include a pressure tube for monitoring pressure at the patient, pressure delivered via nasal cannulae is typically preset and regulated at the pressure source such that excessively low or high pressure at the patient airway is undetectable.

As is known in the art, dangerously high pressures subject the patient to the risk of injury including damage to the lungs and other organs and may lead to additional respiratory complications. On the other hand, excessively low pressure at the patient can drastically reduce the effectiveness of CPAP therapy, especially in the case of neonates and infants wherein the ability to restore and develop full respiratory capability is predicated on the delivery of gas at an appropriate pressure on a constant basis.

Low pressure at the user interface can result from leaks generated between the user interface and the patient's nose and/or mouth. Such leaks may be a result of improper positioning of the user interface on the patient. However, leaks can be generated at the user interface as a result of normal patient movement. Particularly for infants who make frequent jerking and shaking movements as part of their normal physical development, securement of the user interface to the infant's nose and/or mouth is critical in facilitating the delivery of respiratory therapy on a continuous basis at the appropriate pressure.

As can be seen, there exists a need in the art for a user interface for ventilation systems such as CPAP devices which includes a means for maintaining the position of the user interface relative to the patient's nose and/or mouth. Furthermore, there exists a need in the art for a user interface that is comfortable to wear during extended periods of time such that respiratory therapy can be provided to the patient on a continuous and uninterrupted basis despite normal patient movements. Additionally, there exists a need in the art for a fixation mechanism for supporting a tubing member that may be connected to the user interface. Finally, there exists a need in the art for a fixation mechanism which is capable of maintaining the position of the user interface and which is of simple construction, low cost and which is conveniently installable.

BRIEF SUMMARY

The present invention specifically address and alleviates the above-referenced deficiencies associated with user interfaces of the prior art by providing an interface assembly which includes at least one uniquely-configured retainer clip which is specifically adapted to directly anchor at least one tubing member (e.g., a supply tube or a pressure tube of a nasal CPAP device) to a patient such as an infant. An exemplary user interface with which the retainer clip may be utilized is the user interface disclosed in commonly-owned U.S. application Ser. No. 11/241,303 entitled VENTURI GEOMETRY DESIGN FOR FLOW-GENERATOR PATIENT CIRCUIT, the entire contents of which is expressly incorporated by reference herein.

Advantageously, the retainer clip prevents dislodgement of the user interface and loss of sealing engagement with the patient which may compromise the effectiveness of respiratory therapy and create additional health complications for the patient. More specifically, the retainer clip stabilizes the tubing member relative to the patient and thereby maintains the user interface in position on the patient's nose and/or mouth. In addition, the retainer clip provides a means for supporting the tubing member that is connected to the user interface. When used with the user interface, the retainer clip improves patient comfort and thereby improves patient compliance with prescribed ventilation therapy The retainer clip is comprised of a base portion and a clamp portion which may be formed as a unitary structure such as by injection molding. The base portion may be configured as a generally disc-shaped element having a front side and a back side. The clamp portion is disposed on the front side and extends upwardly therefrom and comprises a spaced pair of clamp fingers each having an arcuately-shaped cross section. In this regard, the clamp fingers collectively define a channel into which the tubing member is inserted and contained by frictional fit.

The clamp fingers each have elongate free edges which collectively define a slot that that opens into the channel. The clamp fingers are preferably sized and configured to be resiliently deflectable in order to facilitate insertion of the tubing member through the slot and into the channel. The internal width of the channel is preferably slightly less than an outer diameter of the tubing member in order to provide a frictional fit of the tubing member within the channel. In this manner, axial movement of the tubing member relative to the retainer clip is restricted.

The retainer clip is adapted to be releasably bonded to the patient by means of an adhesive layer that may be applied to the back side of the base portion. The adhesive layer may be applied as a layer of double-faced adhesive tape having pressure-sensitive adhesive on opposing sides of the tape. However, the adhesive layer may also be applied as a fluid such as a gel, liquid of solid adhesive or other suitable configuration.

A preferred material from which the retainer clip may be fabricated is Tuffel III Silicone material commercially available from General Electric. However, any suitable material providing the desired resiliency, strength, and bio-compatibility characteristics may be used. The material is also preferably suitable for injection molding such that the base portion and clamp portion are mass-producible as a unitary structure.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a perspective view of an interface assembly comprising a user interface having a pair of tubing members anchored that are anchored to an infant patient by a retainer clip;

FIG. 2 is a perspective view of the retainer clip illustrating a base portion and a clamp portion that make up the retainer clip and further illustrating a channel extending through the clamp portion for engaging the tubing member;

FIG. 3 is a sectional view taken along lines 3-3 of FIG. 2 and illustrating a slot formed between free edges of a pair of clamp fingers;

FIG. 4 is a perspective view of the retainer clip illustrating a layer of double-faced adhesive tape for releasably adhering the retainer clip to the patient; and FIG. 5 is a plan view of the retainer clip illustrating the clamp portion spanning a width of the base portion.

DETAILED DESCRIPTION

Referring now to the drawings wherein the showings are for purposes of illustrating preferred embodiments of the present invention only, and not for purposes of limiting the same, FIG. 1 perspectively illustrates a user interface 12 mounted to a patient's head 62 and having tubing members 18 extending laterally outwardly from each side of an interface body 14. In the configuration shown, the tubing members 18 extend around the patient's ears 68 and pass over the shoulders 72 of the patient 60 along the jaw 70. Each of the tubing members 18 may be affixed or anchored into place on the patient 60 by means of a uniquely-configured retainer clip 22 mounted on the patient 60 such as on the patient's cheek 74 area as shown in FIG. 1. Advantageously, the retainer clip 22 is configured to anchor the tubing member 18 to the patient 60 and thereby support the tubing member 18 and restrict relative movement of the tubing member 18. By restricting movement of the tubing member 18, movement of the user interface 12 is also thereby minimized which may assist in preventing loss of sealing engagement of the user interface 12.

The user interface 12 as shown in FIG. 1 in a configuration suitable for providing conventional CPAP therapy to the patient 60 as noted by the separate pressure and supply tubes (i.e., tubing members 18) extending from each side of the user interface 12. However, it should be noted that the retainer clip 22 is not limited to supporting and anchoring tubing members 18 for CPAP respiratory devices but is additionally suitable for use with user interfaces 12 for other types of ventilatory treatment. The retainer clip 22 is also suitable for use in administering airborne medication to the patient 60 via the patient's airway. The retainer clip 22 may be used with user interfaces 12 configured as nasal cannulae such as for delivery of CPAP therapy and/or delivery of gasses such as oxygen mixed with room air.

Regardless of the particular embodiment of the user interface 12, the retainer clip 22 is specifically adapted to prevent inadvertent dislodgement of the user interface 12 from the patient's nose 64 and/or mouth 66. In this regard, the retainer clip 22 is configured to be mounted directly to the patient 60 such as on the patient's skin surface and is adapted to restrict movement of the tubing member 18 relative to the patient's face. As indicated above, restriction of movement of the tubing member 18 may, in turn, prevent relative movement of the user interface 12 to which the tubing member 18 is connected. If allowed to occur, movement of the user interface 12 can result in loss of sealing engagement of nostril-engaging stems with the patient nostrils.

Loss of sealing engagement at the user interface 12 at the nose 64 and/or mouth 66 can compromise the effectiveness of CPAP therapy in developing and/or restoring breathing capacity. Particularly in CPAP user interfaces 12 of the type shown in FIG. 1 having a pressure-compensation capability (i.e., via the pressure tube), loss of sealing engagement at the user interface 12 can result in an increase in gas flow through the supply tube. The blower unit may generate increased gas flow through the supply tube in an attempt to maintain a preset pressure at the patient airway. However, an increase in pressure at the patient airway can increase the work of breathing by the patient 60 as well as create other health complications.

Referring to FIGS. 2-5, the retainer clip 22 includes a base portion 24 and a clamp portion 30. The base portion 24 has a back side 26 and a front side 28 with the clamp portion 30 extending outwardly from the front side 28. The base portion 24 is adapted to be mounted on the patient 60 such as directly on the surface of the patient's skin. However, it is also contemplated that the back side 26 may be effectively affixed or mounted to other areas of the patient 60 such on hair-covered areas (e.g., beard, mustache, scalp hair) using an appropriate adhesive, as will be described in greater detail below.

Extending through the clamp portion 30 is an elongate channel 42 that is sized and configured to receive the tubing member 18 such as the supply tube and/or pressure tube illustrated in FIG. 1. The clamp portion 30 may be positioned so as to generally bisect the base portion 24 in a symmetric arrangement although asymmetric positioning of the clamp portion 30 is also contemplated. The channel 42 defines a channel axis indicated by the character reference "A" shown in FIGS. 2 and 5.

The channel axis "A" is shown as being oriented substantially parallel to the back side 26 although non-parallel orientations of the channel axis "A" may be appropriate depending upon the particular geometry and configuration of the user interface 12 from which the tubing members 18 extend. Referring particularly to FIGS. 2-3, the channel 42 is shown as being collectively defined by a spaced pair of clamp fingers 32 extending outwardly from the front side 28. Each one of the clamp fingers 32 has a free edge 34 such that a slot 36 is defined between the free edge 34 of one clamp finger and the free edge 34 of an opposing one of the clamp fingers 32.

As was earlier mentioned, the channel 42 may be adapted to receive the tubing member 18 when inserted thereinto such as through the slot 36. In this regard, at least one of the opposing clamp fingers 32 is configured to be resiliently deflectable in at least an outward direction (i.e., away from the opposing clamp finger). The resiliently outward deflection of the clamp finger facilitates insertion of the tubing member 18 into the channel 42 such as through the slot 36. Furthermore, the clamp fingers 32 are preferably spaced to provide a frictional fit with the tubing member 18 residing within the slot 36. In this regard, the clamp fingers 32 may preferably be sized and configured to be of a slightly smaller dimension than the tubing member 18 prior to inserting into the channel 42.

Additionally, the material from which the retainer clip 22 is formed preferably possesses a desired frictional capability relative to the tubing member 18 to assist in restraining the tubing member 18 within the channel 42. When inserted, the clamp fingers 32 are adapted to capture the tubing member 18 without restricting the free flow of gas passing therethrough.

Each one of the free edges 34 is preferably radiused as shown in FIG. 3 although the free edges 34 may include a chamfer 40 (shown in FIG. 2) in order to facilitate slidable insertion of the tubing member 18 laterally through the slot 36.

Referring more particularly now to FIG. 5, the base portion 24 is shown as being generally disc-shaped. In this regard, the base portion 24 may have a generally circular profile and may be of a generally constant thickness. However, the base portion 24 may assume a variety of shapes, thickness and sizes depending upon the mounting area on the patient 60 and the degree of curvature of the anatomy at the mounting area. For example, when used on the cheek 74 area of smaller-sized patients such as on the infant shown in FIG. 1, the base portion 24 may be of a relatively small width or diameter such as in the range of from about one inch to about two inches in diameter. The base portion 24 may be provided in a relatively larger size if applied to larger adult patients and if mounted on generally larger anatomical areas where there is little curvature.

It is further contemplated that the retainer clips 22 may be provided to support and affix multiple tubing members 18 to the patient 60. In this regard, a plurality of clamp portions 30 may be disposed on or formed with the base portion 24 with each clamp portion 30 defining its own channel 42 for receiving a tubing member 18. The base portion 24 may be provided in a size sufficient for accommodating multiple clamp portions 30 such as in parallel arrangement with one another. It is further contemplated that each one of the clamp portions 30 may be comprised of one of the clamp fingers 32 of an adjacently disposed clamp portion 30. For example, a retainer clip 22 having two clamp portions 30 may include three clamp fingers 32 wherein a middle clamp finger 32 is shared by the two outer clamp fingers 32 so that two tubing members 18 may be secured to the retainer clip 22.

Referring to FIG. 5, it can be seen that each of the clamp portions 30 defines an opposing pair of end portions 38. The clamp portion 30 may be formed on the base portion 24 such that the end portions 38 terminate at a perimeter edge of the base portion 24 such that the clamp portion 30 spans a width of the base portion 24. Alternatively, one of the end portions 38 may extend past the perimeter edge of the base portion 24. In a further embodiment, at least one of the end portions 38 may extend inwardly from the perimeter edge of the base portion 24. In addition, the inner corners of the clamp fingers 32 at the end portions 38 may be chamfered in order to prevent sharp corners that may induce stresses into the tubing member 18 which, over time, may result in cracking or kinking of the tubing member 18.

Referring briefly to FIGS. 3-4, the retainer clip 22 is adapted to releasably adhere to the patient 60 and, in this regard, may include an adhesive layer 44 configured to releasably adhere to the patient's skin. The adhesive layer 44 may be applied to the back side 26 of the base portion 24 as a separately-applied fluid such as a gel, liquid of solid adhesive. More preferably, the adhesive layer 44 comprises adhesive tape having pressure-sensitive adhesive on at least one of opposing sides of the tape.

The adhesive layer 44 may be configured as pressure sensitive tape 46 or as double-faced adhesive tape 48 which is mountable on the back side 26 and which has pressure-sensitive adhesive on each of the opposing sides. An exemplary adhesive tape is commercially available from 3M Corporation under the Designation No. 9177. As shown in FIG. 4, a peel layer 50 may be provided on an exterior side of the double-faced adhesive tape 48 to protect the pressure-sensitive adhesive prior to applying the retainer clip 22 to the patient 60. The double-faced adhesive tape 48 may be comprised of a layer of polymeric foam having pressure-sensitive adhesive on each of its opposing sides and with peel layers 50 covering the pressure-sensitive adhesive.

The back side 26 of the base portion 24 may be planar or flat in order to simplify manufacturing and to facilitate mounting of the adhesive layer 44 to the back side 26. Optionally, the back side 26 may be formed with a slightly concave shape such that the base portion 24 is complementary to the contour of the patient's anatomy proximate the mounting location of the retainer clip 22. Even further, it is contemplated that the back side 26 may be provided in alternative contours including a convex shape or a mixture of other contour shapes including a mixture of the planar and concave shapes mentioned above. The thickness of the base portion 24 is also preferably such that the base portion 24 is deformable to allow the base portion 24 to better conform to contours of the patient's anatomy and to facilitate bonding of the retainer clip 22 to the patient's skin.

Regarding materials from which the retainer clip 22 may be fabricated, any suitable material such as polymeric material may be used. A preferred material is Tuffel III Silicone material commercially available from General Electric. However, any suitable bio-compatible material may be used if the material provides the desired resiliency characteristics to the clamp fingers 32. In addition, the material is preferably compatible with the adhesive that is applied to the back side 26. Furthermore, the material is preferably suitable for injection molding or by other suitable forming process such that the base portion 24 and clamp portion 30 may be mass produced in an economical manner as a unitary structure. Exemplary materials for forming the retainer clip 22 include, but are not limited to, silicone and/or rubber material, polyethylene, polyvinyl and/or polyester material or any combination thereof.

The retainer clip 22 may be included as at least one of the components of an interface assembly 10 as part of a breathing device for delivering respiratory therapy from a gas source 16 to a patient 60 as illustrated in FIG. 1. The interface assembly 10 may further comprise the user interface 12 (e.g., nasal mask, nasal prongs) and at least one tubing member 18. The user interface 12 is preferably sized and configured to engage at least one of the patient's nose 64 and mouth 66 and may be configured as the nasal cannulae mentioned above or as nasal pillows, nasal prongs and nasal mask or any other suitable configuration. The tubing member 18 may comprise any hollow fluid conduit such as may be used to delivering oxygenated air, medication or other fluids to the patient 60 and/or for providing pressurized gas to the patient 60 using the supply tube illustrated in FIG. 1. In addition, the tubing member 18 may be adapted to fluidly communicate pressure for purposes of monitoring and/or regulating pressure at the patient airway as provided by the pressure tube illustrated in FIG. 1.

The use of the retainer clip 22 will now be described with reference to the figures wherein FIG. 1 illustrates the interface assembly 10 comprising the user interface 12, at least one tubing member 18 (e.g., supply tube, pressure tube) extending therefrom, and at least one retainer clip 22 adapted to affix or anchor the tubing member 18 to the patient 60 such as on the cheek 74 area as illustrated. The tubing members may be joined together such as via a band 20 as illustrated in FIG. 1. As described above, the tubing member 18 is releasably insertable into the channel 42 by passing the tubing member 18 through the slot 36. The clamp fingers 32 are specifically adapted to resiliently deflect outwardly as the tubing member 18 is inserted into the channel 42 whereupon the clamp fingers 32 return to the non-deflected position and clamp the tubing member 18 in the channel 42. Ideally, the spacing between the clamp fingers 32 is such that the tubing member 18 is captured within the clamp portion 30 by frictional fit between an outer wall of the tubing member 18 and inner surfaces of the clamp fingers 32.

Once inserted, the retainer clip 22 may be positioned in spaced relation to the user interface 12 such that when the user interface 12 is placed in sealing engagement with the patient's nose 64 and/or mouth 66, the retainer clip 22 is located proximate the desired mounting area on the patient 60 such as proximate the cheek 74 area as illustrated in FIG. 1. Adhesive is either pre-applied to the back side 26 of the base portion 24 or the user (e.g., nurse, physician, etc.) applies a suitable adhesive such as a medical grade adhesive layer 44 to the back side 26. As was mentioned above, the adhesive layer 44 may preferably comprise a layer of double-faced adhesive tape 48 which may include the peel layer 50 covering pressure-sensitive adhesive. To improve the bond, the desired mounting area may optionally be wiped with a solvent such as alcohol to remove dirt, oil and other debris that may interfere with the adhesion.

To mount the retainer clip 22 to the patient 60, the peel layer 50 is removed and the back side 26 of the retainer clip 22 is applied to the patient's skin surface at the desired attachment point until the adhesive layer 44 adheres thereto. For user interfaces 12 having two or more tubing members 18 (e.g., pressure and supply tubes), retainer clips 22 are mounted on each tubing member 18 and positioned a desired distance away from the user interface 12 prior to adhering the retainer clips 22 to the patient 60.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A retainer clip adapted to affix a tubing member to a patient, the retainer clip comprising:
    a rounded base portion having a round back side and a round front side; and
    at least one clamp portion extending outwardly from the front side and extending a width of said rounded base portion such that a first end portion and a second end portion terminate at a perimeter edge of said rounded base portion, the at least one clamp portion defining a channel extending therethrough said front side, the channel being sized and configured to not completely encapsulate the tubing member at said clamp portion and configured to releasably receive the tubing member and configured to bisect the front side of said rounded base portion,
    wherein said channel prevents the tubing member from contacting said rounded base portion, wherein at least a portion of the round back side is configured to releasably adhere to the patient, wherein said rounded base portion and said clamp portion are of the same uniform thickness, and wherein at least one of the first end portion or the second end portion comprises a chamfer on an arcuate edge adjacent to the channel.

2. The retainer clip of claim 1 wherein the clamp portion comprises a plurality of clamp fingers disposed in parallel relation to one another.

3. The retainer clip of claim 1 wherein the clamp portion includes a spaced pair of clamp fingers extending outwardly from the front side, the clamp fingers being spaced to provide a frictional fit with the tubing member.

4. The retainer clip of claim 1 wherein at least a portion of the back side is covered with an adhesive layer configured to adhere to the patient's skin.

5. The retainer clip of claim 1 wherein the adhesive layer comprises adhesive tape disposed on the back side and including pressure-sensitive adhesive adapted to releasably adhere to the patient's skin.

6. The retainer clip of claim 1 wherein the base and clamp portions are fabricated of a polymeric material.

7. A retainer clip adapted to affix a tubing member to a patient, the retainer clip comprising:
   a rounded base portion having a round back side and a round front side; and
   a clamp portion including a spaced pair of clamp fingers extending outwardly from the front side and extending a width of said rounded base portion such that a first end portion and a second end portion of the spaced pair of clamp fingers terminate at a perimeter edge of said rounded base portion, each one of the clamp fingers having a free edge, the free edges collectively defining a slot therebetween, the clamp fingers collectively defining a channel having a channel axis oriented substantially parallel to the back side, the channel being sized and configured to not completely encapsulate the tubing member at said clamp portion and configured to bisect the front side of said rounded base portion, wherein said clamp fingers prevent the tubing member from contacting said rounded base portion;
   wherein:
   at least one of the opposing clamp fingers is configured to be resiliently outwardly deflectable to facilitate insertion of the tubing member into the channel through the slot;
   at least a portion of the back side is configured to releasably adhere to the patient and wherein said rounded base portion and said clamp portion are of the same uniform thickness; and
   at least one of the first end portion or the second end portion comprises a chamfer on an arcuate edge adjacent to the channel.

8. The retainer clip of claim 7 wherein the clamp portion comprises a plurality of clamping fingers disposed in parallel relation to one another.

9. The retainer clip of claim 7 wherein the clamp fingers are spaced to provide a frictional fit with the tubing member.

10. The retainer clip of claim 7 wherein at least a portion of the back side is covered with adhesive tape having pressure-sensitive adhesive adapted to releasably adhere to the patient's skin.

11. The retainer clip of claim 7 wherein the back side has a contour configured to be complementary to the patient's anatomy proximate a mounting location of the retainer clip.

12. The retainer clip of claim 7 wherein the base and clamp portions are fabricated of a polymeric material.

13. An interface assembly for delivering gas from a gas source to a patient, comprising:
    a user interface sized and configure to engage at least one of the patient's nares;
    at least one tubing member extending laterally outwardly from the user interface; and
    at least one retainer clip having a rounded base portion and a clamp portion, said rounded base portion having a round back side and a round front side, the clamp portion being disposed outwardly on the front side and being disposed a width of said rounded base portion such that a first end portion and a second end portion terminate at a perimeter edge of the rounded base portion, the clamp portion defining a channel oriented substantially parallel to the back side, the channel being sized and configured to not completely encapsulate the at least one tubing member at said retainer clip and configured to receive the at least one tubing member and configured to bisect the front side of said rounded base portion, the back side being configured to releasably adhere to the patient, wherein said clamp portion prevents the at least one tubing member from contacting said rounded base portion and wherein said rounded base portion and said clamp portion are of the same uniform thickness, and wherein at least one of the first end portion or the second end portion comprises a chamfer on an arcuate edge adjacent to the channel.

14. The interface assembly of claim 13 wherein the clamp portion comprises a plurality of clamp fingers disposed in parallel relation to one another.

15. The interface assembly of claim 13 wherein the clamp portion includes a plurality of clamp fingers that are spaced to provide a frictional fit with the at least one tubing member.

16. The interface assembly of claim 13 wherein the back side has a contour configured to be complementary to the patient's anatomy proximate a mounting location of the retainer clip.

17. The interface assembly of claim 13 wherein at least a portion of the back side is covered with an adhesive layer configured to adhere to the patient's skin.

18. The interface assembly of claim 17 wherein the adhesive layer comprises adhesive tape disposed on the back side and including pressure-sensitive adhesive adapted to releasably adhere to the patient's skin.

19. The interface assembly of claim 13 wherein the base and clamp portions are fabricated of a polymeric material.

* * * * *